United States Patent [19]

Kaul et al.

[11] Patent Number: 5,008,921
[45] Date of Patent: Apr. 16, 1991

[54] PORTABLE X-RAY DIAGNOSTICS APPARATUS WITH POSITION-ADJUSTABLE CONTROL PANEL

[75] Inventors: Karlheinz Kaul; Hans-Christian Bock, both of Uttenreuth, Fed. Rep. of Germany

[73] Assignee: Siemens Aktiengesellschaft, Berlin and Munich, Fed. Rep. of Germany

[21] Appl. No.: 411,737

[22] Filed: Sep. 25, 1989

[30] Foreign Application Priority Data

Oct. 11, 1988 [EP] European Pat. Off. ........ 88116873.6

[51] Int. Cl.⁵ ............................................. H05G 1/02
[52] U.S. Cl. .................................... 378/198; 378/193
[58] Field of Search ................ 378/195, 196, 197, 198

[56] References Cited

U.S. PATENT DOCUMENTS

| 3,971,946 | 7/1976 | Craig et al. | 38/195 |
| 4,802,197 | 1/1989 | Juergens | 378/198 |

FOREIGN PATENT DOCUMENTS

| 0244561 | 11/1987 | European Pat. Off. |
| 3138916 | 4/1983 | Fed. Rep. of Germany |
| 8521246 | 2/1986 | Fed. Rep. of Germany |
| 1269786 | 7/1980 | France |
| 2192591 | 1/1988 | United Kingdom |

OTHER PUBLICATIONS

Siemens "SIREMOBIL 4" Brochure.

*Primary Examiner*—Craig E. Church
*Attorney, Agent, or Firm*—Hill, Van Santen, Steadman & Simpson

[57] ABSTRACT

A portable x-ray diagnostics apparatus has a base to which a support for an x-ray tube and an x-ray detector is mounted at a front of the base. A control panel for operating the x-ray apparatus is electrically connected to compnents in the interior of the base by a flexible cable. The length of the cable permits the position of the control panel relative to the base to be selected as being at a rear of the base, or at either side of the base, so that the control panel can be positioned so as to be easily read or reached by a user. The top surface of the base may have recesses therein adapted to receive and releasably hold the control panel in the various positions, or the control panel may be magnetically held on the top surface at a selected position.

5 Claims, 1 Drawing Sheet

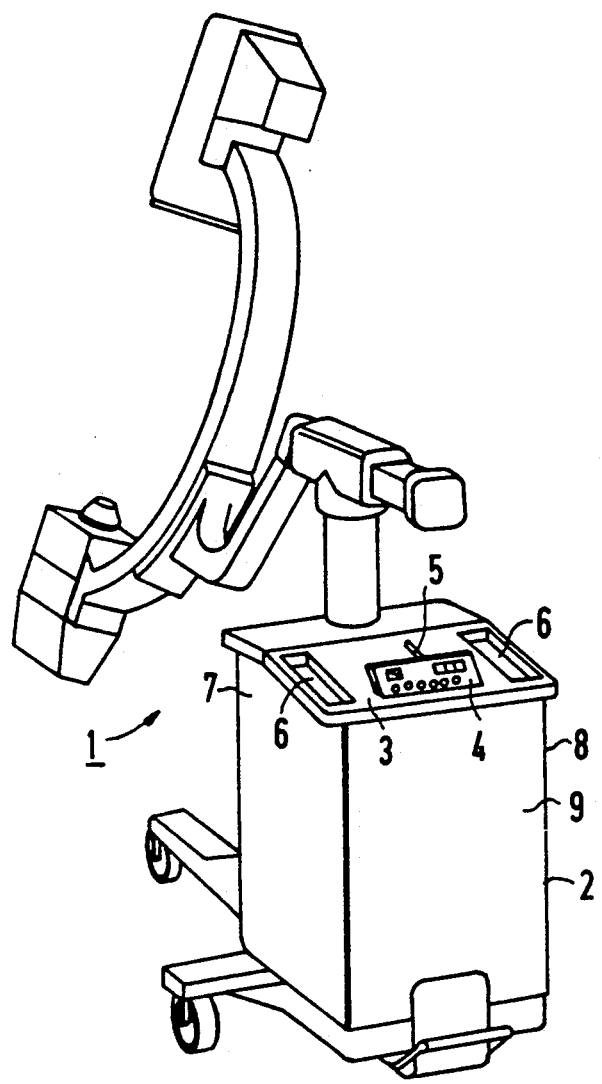

PORTABLE X-RAY DIAGNOSTICS APPARATUS WITH POSITION-ADJUSTABLE CONTROL PANEL

BACKGROUND OF THE INVENTION

1. Field of the Invention

The present invention is directed to a portable x-ray diagnostics apparatus, and in particular to such an apparatus wherein the control panel can be placed at various positions as be best suited to the location of the operator of the apparatus.

2. Description of the Prior Art

A commercially available portable x-ray diagnostics apparatus is described in the Siemens publication "Siremobil 4" which has a control panel rigidly contained in an upper wall or surface of a base or control box of the apparatus. The control panel is positioned so that it can be most easily read and operated at the rear of the x-ray diagnostics apparatus.

The orientation of the control panel is such that reading the displays thereon, and actuating the operating controls thereon, is difficult from a location other than the rear of the x-ray diagnostics apparatus, such as at the sides of the apparatus.

A portable x-ray apparatus is described in German Gebrauchsmuster 8 521 246 wherein a control panel or box is suspended from a boom attached to the top of a vertical column extending from the base of the apparatus. The control box is suspended at eye level, and is pivot around a vertical axis with the boom, so that the control can be pivoted into a position favorable for the operator example, at the rear or at the sides of the apparatus. Kingdom published application No. 2 192 591 discloses a having a control box which can be rotated around a axis at an upper side of a housing for the unit, so that a comfortable actuation of the keyboard is possible at each of the printer. The control box can be removed from the side of the housing, so that the keyboard can also be operated from a position remote from the printer.

SUMMARY OF THE INVENTION

The base is freely moveable, which as used herein means that the base is not attached, permanently or otherwise, to the floor, ceiling or walls of the room in which the base is disposed. This is intended to distinguish the device disclosed herein from units permanently attached to a structural element of a room or a building.

It is an object of present invention to provide a portable x-ray diagnostics apparatus wherein the control panel is adjustably mountable to the apparatus so that an easy operation of the controls and reading of the displays is possible at the sides the x-ray diagnostics apparatus, as well as at the rear of the apparatus.

The above object is achieved in accordance with the principles of the present invention in a portable x-ray diagnostics apparatus wherein respective mounts for the control panel are provided at an upper of the base of the apparatus, which permit the control to be mounted in defined positions parallel to the rear end face of the apparatus and parallel to the side faces of the apparatus.

The operating comfort is significantly increased, because the control panel can then be positioned at any one of three sides of the unit, to accommodate the location at which the operator of the apparatus is standing.

The control panel can arranged parallel to either side of the apparatus or parallel to the rear face of the apparatus, mounted on the control box or base of the apparatus.

DESCRIPTION OF THE DRAWINGS

The single FIGURE is a perspective view, from the rear and to one side, of a portable x-ray diagnostics apparatus constructed in accordance with the of the present invention.

DESCRIPTION OF THE PREFERRED EMBODIMENTS

A portable x-ray apparatus 1 is shown in the drawing which includes a control box or base 2 having an upper surface 3 on which a control panel 4 is mounted in a position-adjustable manner, as described below. The control panel is connected to the base 2 by a flexible cable 5. In addition to permitting the position of the control panel 4 to be freely adjusted, the cable 5 is also of a length selected to prevent the control panel 4 from falling off of the upper surface 3 of the base 2.

The base 2 has a support extending from a front thereof for an x-ray tube and an x-ray detector. The base 2 has a rear wall 9 and opposite side 7 and 8. The control panel 4 can be releasably mounted at positions on the upper surface 3 so that the control panel can be easily read, and the controls thereon easily manipulated, by an operator standing so as to face either sides 7 or 8, or facing the rear wall 9. The control panel 4 may be placed, for example, parallel to any one of those sides. The control panel 4 is held in place at the various positions by, for example, recesses 6 in the upper surface 3. In the drawing, two empty recesses 6 can be seen parallel to sides 7 and 8, and the control panel 4 is disposed in an identical recess parallel to the rear wall 9. Alternatively, or in addition to the recesses 6, one or more permanent magnets may be affixed to the back of the control panel 4, with the upper surface 3 of the base 2 consisting, at least in regions where it is desired to place the control panel 4, of magnetically attractive material.

Although modification and changes may be suggested by those skilled in the art, it is the intention of the inventors to embody within the patent warranted hereon all changes and modifications as reasonably and properly come within the scope of their contribution to the art.

We claim as an invention:

1. A mobile x-ray diagnostics apparatus comprising:
    an x-ray source and an x-ray detector and means for supporting said x-ray source and x-ray detector;
    a freely moveable base having a front portion to which said means for supporting is attached, and having a rear and left and right sides and a top surface;
    a control panel for operating said apparatus; and
    a plurality of mounting locations disposed on said upper surface of said base for releasably holding said control panel in place on said upper surface substantially parallel to a selected one of said right side, said left side or said rear of said base so that an operator can operate said apparatus via said control panel while standing adjacent said base.

2. A mobile x-ray diagnostics apparatus as claimed in claim 1, further comprising:
    a flexible cable connecting said control panel to said base, said cable having a length which prevents said control box from falling off of said upper surface of said base.

3. A mobile x-ray diagnostics apparatus as claimed in claim 1, wherein said mounting locations on said upper surface of said base are a plurality of recesses in said upper surface, corresponding in size to the size of said control panel, in which said control panel can be placed and held.

4. A mobile x-ray diagnostics apparatus as claimed in claim 1, wherein said control panel has a back with a permanent magnet affixed thereto, and wherein said mounting locations are magnetically attractive locations of said upper surface of said base.

5. A mobile x-ray diagnostics apparatus as claimed in claim 1, wherein said control panel is held by means of a permanent magnet at said upper surface of said base.

* * * * *